United States Patent [19]

Hurson et al.

[11] Patent Number: 5,030,096
[45] Date of Patent: Jul. 9, 1991

[54] IMPLANT HEALING CAP AND HOLDER

[75] Inventors: Steven M. Hurson, El Toro; John J. Burgardt, Huntington Beach, both of Calif.

[73] Assignee: Steri-Oss, Inc., Anaheim, Calif.

[21] Appl. No.: 415,977

[22] Filed: Oct. 2, 1989

[51] Int. Cl.⁵ ............................................. A61C 3/00
[52] U.S. Cl. .................................. 433/173; 433/141
[58] Field of Search ............... 433/141, 173, 174, 175, 433/176

[56] References Cited

U.S. PATENT DOCUMENTS

| | | | |
|---|---|---|---|
| 2,347,567 | 4/1944 | Kresse | 433/174 |
| 3,690,005 | 9/1972 | Edelman | 433/187 |
| 4,177,562 | 12/1979 | Miller et al. | 433/174 |
| 4,187,609 | 2/1980 | Edelman | 433/176 |

FOREIGN PATENT DOCUMENTS

| | | | |
|---|---|---|---|
| 0131831 | 1/1985 | European Pat. Off. | 433/176 |
| 2812250 | 10/1978 | Fed. Rep. of Germany | 433/176 |
| 2596273 | 10/1987 | France | 433/173 |

*Primary Examiner*—Cary E. Stone
*Assistant Examiner*—Adriene B. Lepiane
*Attorney, Agent, or Firm*—Grant L. Hubbard

[57] ABSTRACT

A dental implant installation assembly which comprises three components, first, a dental implant having a biocompatible surface, a first end for being located in the alveolar cavity and a second end having formed therein a threaded opening, second a protective cap screw in the threaded opening in the implant, the screw having formed therein a female wrench-engaging cavity constructed and adapted to engage an insertable wrench, and, third, a holder having a gripping portion and a holding projection received in compression in the wrench-engaging cavity of the cap screw, the holder being releasable from the cap screw when the holder is bent relative to the head thereof is disclosed.

3 Claims, 1 Drawing Sheet

IMPLANT HEALING CAP AND HOLDER

BACKGROUND OF THE INVENTION

Dental implants are in common use to provide a holding system for a new tooth. Typically, the dental implant comprises an elongate body which has a biocompatible surface and may be made entirely of a biocompatible alloy or material. The typical implant has the first end which is constructed and adapted to be inserted into and screwed into the alveolar cavity in the jawbone. A variety of structures, surfaces, and screw designs have been provided in the prior art. One very satisfactory dental implant is described in U.S. patent application Ser. No. 346,080 and in U.S. patent application Ser. No. 921,351.

It is common practice to install the dental implant in the alveolar cavity in the jawbone and place a temporary cap on the implant for a period of a few weeks while healing takes place and to permit the tissue to grow into and bond to the threads and structure of the implant before the tooth-cap is actually installed on the implant, thus avoiding the forces of chewing which might prevent proper healing and bonding of the implant if the tooth were installed immediately.

Many implants are simply pressed into the alveolar cavity while others are screwed into the cavity. Regardless of the method of installing the implant, immediately after the installation, the implant is inserted into the alveolar cavity with the second end, which has formed therein a threaded opening, extending to the cortical plate. A cap serves as a protective device during healing and prevents the tissue from growing into the interior of the opening of the implant. One known approach is to place a screw with a cap or a sleeve on the top of it into the threaded opening in the second end of the dental implant.

A major difficulty faced by the surgeon or dentist is in the handling of the implant inside the patient's mouth. It is to this problem that the present invention is directed.

SUMMARY OF THE INVENTION

In a convenient embodiment, the invention comprises a kit for performing dental implants comprising a dental implant having a biocompatible surface, a first end which is constructed and adapted to be located within the interior of the alveolar cavity, and a second end which is adapted to be secured to a prosthesis, said second end having formed therein a threaded opening. An implant protective cap screw having a threaded portion constructed is screwed into the threaded opening in the implant. The cap screw has a head approximately the size of the second end of the dental implant for sealing the opening in the second end against tissue ingrowth during the initial healing period following installation of the implant into a patient. The head of the cap screw has formed therein a female wrench-engaging cavity constructed and adapted to engage an insertable wrench for turning the cap screw. A holder is provided for holding and installing the cap screw and dental implant, said holder comprising a gripping portion for permitting the dentist or surgeon to grip the holder, and a resilient cap screw holding projection constructed and configured to be received in compression in the wrench-engaging cavity of the cap screw for supporting the cap screw and implant during installation and for releasing the cap screw when the holder is bent relative to the head thereof.

The invention is also embodied in a method for installing dental implants which comprise a biocompatible surface, a first end which is constructed and adapted to be located within the interior of the alveolar cavity, and a second end which has formed therein a threaded opening and is adapted to be secured to a prosthesis. According to the method, the user, i.e. the dentist or surgeon, supports a protective cap screw received in the threaded opening in the implant, said cap screw having a head approximately the size of the second end of the dental implant for sealing the opening in said second end, the head of the cap screw having formed therein a female wrench-engaging cavity constructed and adapted to engage an insertable wrench for turning the cap screw, on a holder comprising a gripping portion for permitting the dentist or surgeon to grip the holder, and a resilient cap screw holding projection constructed and configured to be received in compression in the wrench-engaging cavity of the cap screw. After inserting the implant thus supported into the alveolar cavity, the cap screw is released from the holder by bending the holder relative to the head of the cap screw.

The invention may also be embodied in a dental implant installation assembly which comprises three components. First, a dental implant is provided having a biocompatible surface, a first end which is constructed and adapted to be located within the interior of the alveolar cavity, and a second end which is adapted to be secured to a prosthesis, said second end having formed therein a threaded opening. Secondly, an implant protective cap screw is inserted into and threaded into the threaded opening in the implant, said screw having a head approximately the size of the second end of the dental implant, the head of the cap screw having formed therein a female wrench-engaging cavity constructed and adapted to engage an insertable wrench for turning the cap screw. The third component is a holder having a gripping portion for permitting the dentist or surgeon to grip the holder by means of a resilient cap screw holding projection received in compression in the wrench-engaging cavity of the cap screw, said holder being releasable from the cap screw when the holder is bent relative to the head thereof.

DESCRIPTION OF THE PREFERRED EMBODIMENT

Figure 1:
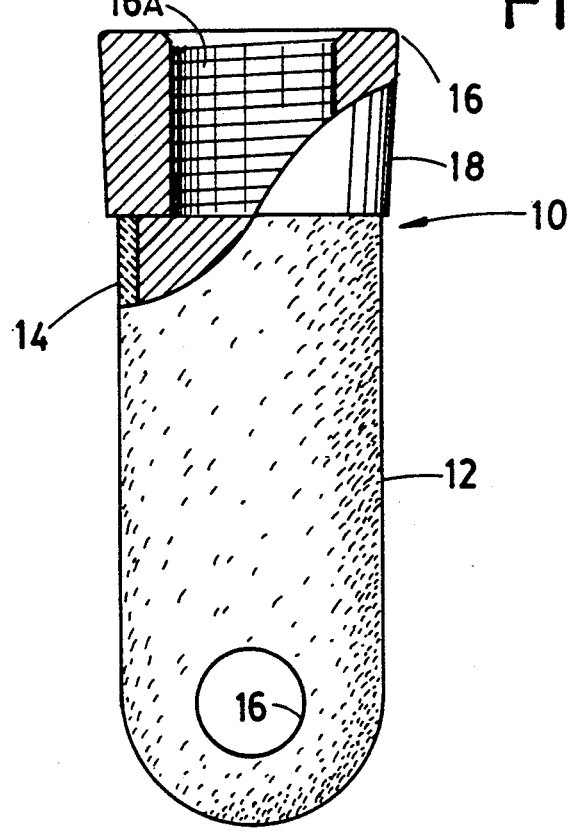
FIG. 1 is a side view, in partial cross-section, of the second end and the first end of a dental implant with which this invention may be used.

While this invention may be used with any of a great variety of dental implants, a very satisfactory and widely used dental implant is shown in FIG. 1. The dental implant 10 has a biocompatible surface which is indicated generally at 12. The structure of the surface may be of any biologically compatible structure, but is preferably formed of a hydroxyapatite layer 14 such as is described in my patent application filed contemporaneously herewith. The dental implant comprises a first end, which is shown coated with hydroxyapatite and having a passage 15 formed therethrough to permit in-growth of bone and tissue for locking the implant in place following installation. A threaded biologically compatible first end or any other first end which is suitable for implantation may be used. A second end 16, which is shown in partial cross-section in FIG. 1, is provided with a threaded opening 16$_A$.

Figure 2:
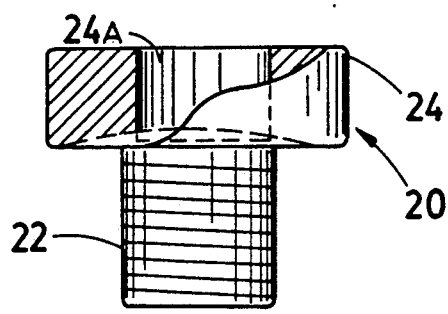
FIG. 2 is a side view, in partial cross-section, of the protective cap screw of this invention.

The cap screw 20 of this invention, shown in partial cross-section in FIG. 2, comprises a threaded portion 22 which is sized, constructed and configured to be threadably received in the threaded opening 16$_A$ on the second end of the dental implant 10. The cap screw also includes a head 24 which is approximately the diameter of the second end of the dental implant. By being approximately the size of the second end of the dental implant, it is meant that the head will cover all or substantially all of the second end of the dental implant and may extend outwardly beyond the diameter of the dental implant. The head may also have formed therein a frusto-concave lower surface around the threaded portion for engaging the implant 10. The term frusto-concave as used here means that the bottom surface generally is concave, approximately arcuately formed, except that the center of any arc is interrupted by the presence of the threaded portion. This permits the cap to seal tightly along its periphery to the second end of the implant. Screws generally of this type may comprise a skirt or other structure which may extend down over a small portion of the sides of the dental implant. Since the precise construction of the head, insofar as it covers and protects the dental implant is concerned, is not critical, no particular configuration is connoted by the drawing. Inside the head 24 of the screw cap, a cavity 24$_A$ is formed and is adapted to receive an insertable wrench, such as an Allen wrench, spline wrench, or any of the various kinds of wrenches or tools which are inserted into a cavity and, by the size and configurational relationship, can be used to rotate the body in which the cavity is formed. The Allen wrench will be referred to hereinafter simply because it is very commonly used and is well known, although the precise configuration of the wrench and the cavity are not important, so long as they permit the wrench to turn the screw.

Figure 3:
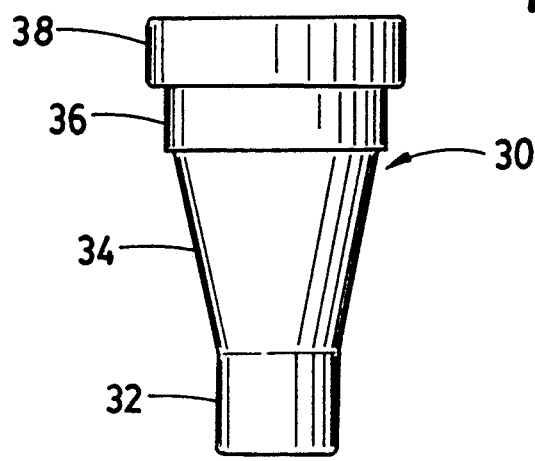
FIG. 3 is a side view of the cap screw holder of this invention.

An important feature of the invention is the holder 30 and, in particular, the holding projection 32, as shown in FIG. 3. The holder also comprises what may be referred to as a transition portion 34 and, if desired, may include a slidable engaging portion 36 for being received inside a shipping vial and a cap 38 for the vial for mounting the assembly of implant 10, cap screw 20, and holder 30 against damage by shock, etc., during handling and shipping. Devices generally of this type are shown in U.S. patent application Ser. No. 140,255 and, insofar as fitting into a particular container or forming a cap therefor, form no part of the present invention. All that is necessary is that a gripping portion be formed, as, in the present instance, by the cap 38, although all of these structures are not required. Any configuration of the gripping portion is quite satisfactory so long as it permits the dentist or surgeon to grip and hold the screw holder firmly.

During use, the dentist or surgeon installs the dental implant. The first end is constructed and adapted to be located within the interior of the alveolar cavity and is installed into the cavity by the surgeon or dentist who simply holds the holder, positions the implant, pushes it into position, and, by bending the holder to one side, removes the holding projection 32 from the cavity 24$_A$.

It is the mechanism and method of supporting the protective cap screw and implant with the holder, the head of the cap screw having formed therein a female wrench-engaging cavity, and the resilient cap screw holding projection received in compression in the wrench-engaging cavity of the cap screw to which this invention is directed. The projection is made of a resilient material, such as any of a great many polymers. Not a great deal of resilience is required, and most of the commonly used polymers may be used in constructing the holder of this invention. The vinyl polymers generally, polyethylene, polypropylene, nylon, etc., are suitable polymers. The resilient projection may also be formed of a natural polymer, but the synthetic polymers are preferred because the material is more uniform and is safely sterilized. The resilient projection could also be formed of metal, using, for example, a spring steel projection of suitable size with sufficient space to permit compression within the spring. As indicated, however, the preferred method of carrying out the invention is simply to injection mold or otherwise form a holder with the projection thereon of a suitable polymer.

With the cap screw and implant thus supported, the holder is inserted into the patient's mouth. Once the implant with cap screw is satisfactorily received and seated, the holder is removed simply by bending it to the side relative to the cap screw. This releases the projection from its compressed engagement inside the cavity of the cap screw, leaving the cap screw and implant in proper location, there having been no force tending to withdraw the implant exerted during removal of the holder.

The invention is conveniently embodied in a kit which includes the implant, the cap screw, and the holder, along with such other devices as may be necessary such as, for example, Allen wrenches, etc.

In another convenient embodiment, the invention may be described as a method of installing cap screws in dental implants, as has been previously described.

It will be understood that the foregoing description is of the preferred embodiment of the invention, and, within the scope of the disclosure and the claims which follow, a great many variations in the structure and configuration and materials of which the various components may be formed is permitted without departing from the spirit and scope of the invention as defined in the claims.

INDUSTRIAL APPLICATION

This invention is useful in the dental arts and in the manufacture to dental appliances.

What is claimed is:

1. A kit for performing dental implants comprising:
   a dental implant having a biocompatible surface, a first end which is constructed and adapted to be located within the interior of the alveolar cavity, and a second end which is adapted to be secured to a prosthesis, said second end having formed therein a threaded opening;
   an implant protective cap screw having a threaded portion constructed and adapted to be screwed into the threaded opening in the implant, and a head approximately the size of the second end of the dental implant for sealing the opening in said second end against tissue ingrowth during the initial healing period following installation of the implant into a patient, the head of the cap screw having formed therein a female wrench-engaging cavity constructed and adapted to engage an insertable wrench for turning the cap screw; and a holder for holding and installing the cap screw and dental implant, said holder comprising a gripping portion for permitting the dentist or surgeon to grip the holder, and a resilient cap screw holding projection constructed and configured to be received in compression in the wrench-engaging cavity of the cap screw for supporting the cap screw and implant during installation and for releasing the cap screw when the holder is bent relative to the head thereof.

2. A method for installing dental implants which comprise a biocompatible surface, a first end which is constructed and adapted to be located within the interior of the alveolar cavity, and a second end which has formed therein a threaded opening and is adapted to be secured to a prosthesis, the method comprising the steps of:

supporting a protective cap screw received in threaded opening in the implant, said cap screw having a head approximately the size of the second end of the dental implant for sealing the opening in said second end, the head of the cap screw having formed therein a female wrench-engaging cavity constructed and adapted to engage an insertable wrench for turning the cap screw, on a holder comprising a gripping portion for permitting the dentist or surgeon to grip the holder, and a resilient cap screw holding projection constructed and configured to be received in compression in the wrench-engaging cavity of the cap screw;

inserting the implant thus supported into the alveolar cavity; and releasing the cap screw by bending the holder relative to the head of the cap screw.

3. A dental implant installation assembly comprising:

a dental implant having a biocompatible surface, a first end which is constructed and adapted to be located within the interior of the alveolar cavity, and a second end which is adapted to be secured to a prosthesis, said second end having formed therein a threaded opening;

an implant protective cap screw inserted into and threaded into the threaded opening in the implant, said screw having a head approximately the size of the second end of the dental implant, the head of the cap screw having formed therein a female wrench-engaging cavity constructed and adapted to engage an insertable wrench for turning the cap screw; and a holder having a gripping portion for permitting the dentist or surgeon to grip the holder by means of a resilient cap screw holding projection received in compression in the wrench-engaging cavity of the cap screw, said holder being releasable from the cap screw when the holder is bent relative to the head thereof.

* * * * *